(12) United States Patent
Huffer et al.

(10) Patent No.: US 9,278,796 B2
(45) Date of Patent: Mar. 8, 2016

(54) CONTAINER HAVING SELF-CONTAINED HEATER MATERIAL

(71) Applicant: SONOCO DEVELOPMENT, INC., Hartsville, SC (US)

(72) Inventors: Scott William Huffer, Hartsville, SC (US); Adam Laubach, College Station, TX (US); Darko Marquez, College Station, TX (US); Christopher S. Pedicini, Nashville, TN (US)

(73) Assignees: Sonoco Development, Inc., Hartsville, SC (US); Rechargeable Battery Corporation, College Station, TX (US)

( * ) Notice: Subject to any disclaimer, the term of this patent is extended or adjusted under 35 U.S.C. 154(b) by 0 days.

(21) Appl. No.: 14/621,768

(22) Filed: Feb. 13, 2015

(65) Prior Publication Data

US 2015/0232254 A1 Aug. 20, 2015

Related U.S. Application Data

(63) Continuation-in-part of application No. 14/182,034, filed on Feb. 17, 2014, now Pat. No. 9,024,360.

(51) Int. Cl.
*B65B 9/04* (2006.01)
*B65D 65/40* (2006.01)
(Continued)

(52) U.S. Cl.
CPC ............ *B65D 81/3484* (2013.01); *B65D 65/14* (2013.01); *B65D 65/40* (2013.01); *B65D 75/5827* (2013.01); *B65D 75/5855* (2013.01); *B65D 2565/388* (2013.01)

(58) Field of Classification Search
CPC ........ B31B 2221/05; B31B 1/62; B31B 1/64; B65B 9/04; B65B 31/04; B65D 2565/388; B65D 27/005; B65D 65/40; B65D 81/3484; F24J 1/00
See application file for complete search history.

(56) References Cited

U.S. PATENT DOCUMENTS 4,874,656 A 10/1989 Rantanen
5,919,547 A 7/1999 Kocher et al.
(Continued)

FOREIGN PATENT DOCUMENTS

EP 1 164 093 A1 12/2001
WO WO 2008/086388 A1 7/2008
WO WO 2012/008064 A1 1/2012

OTHER PUBLICATIONS

Dellarocca, P.; "*Air-Activated Ration Heaters;*" Proceedings of the Army Science Conference (26th); dated Dec. 2008.
(Continued)

*Primary Examiner* — Evan Pert
*Assistant Examiner* — Gustavo Ramallo
(74) *Attorney, Agent, or Firm* — Alston & Bird LLP

(57) ABSTRACT

A container is provided that has a compartment for storing an air-activated material for heating contents. The compartment is formed between a first web of material and a second web of material. The first web includes a first film layer laminated to a second film layer. A portion of the first film layer of the first web can be separated from the second film layer to reveal openings in the first film layer that allow air to enter the compartment. When the air contacts the air-activated material to activate the material, an exothermic reaction takes place that serves to produce heat, such as to heat the contents of the container. Prior to separation of the first and second film layers, the container is designed to allow ingress of oxygen into the compartment at a rate less than approximately 3 cc per 100 in$^2$ per 24 hrs. at 23° C.

18 Claims, 5 Drawing Sheets

(51) Int. Cl.
*B65D 81/34* (2006.01)
*B65D 65/14* (2006.01)
*B65D 75/58* (2006.01)

(56) References Cited

U.S. PATENT DOCUMENTS

| | | | |
|---|---|---|---|
| 6,974,612 B1* | 12/2005 | Frisk | B32B 27/10 |
| | | | 428/34.1 |
| 8,192,120 B1* | 6/2012 | Gess | B60P 7/065 |
| | | | 410/119 |
| 2004/0006950 A1 | 1/2004 | Knoerzer et al. | |
| 2004/0211698 A1 | 10/2004 | John Mak | |
| 2005/0006383 A1* | 1/2005 | Watkins | B65D 81/3453 |
| | | | 219/759 |
| 2007/0007229 A1 | 1/2007 | Yousif | |
| 2007/0202284 A1 | 8/2007 | True | |
| 2008/0128431 A1 | 6/2008 | Gradzewicz | |
| 2010/0163011 A1 | 7/2010 | Tinker et al. | |
| 2010/0278454 A1 | 11/2010 | Huffer | |
| 2010/0326418 A1 | 12/2010 | Sesock et al. | |
| 2011/0081460 A1 | 4/2011 | Becraft et al. | |
| 2011/0103718 A1 | 5/2011 | Bosman | |
| 2011/0204054 A1 | 8/2011 | Huffer | |
| 2013/0174835 A1 | 7/2013 | Tinker et al. | |
| 2013/0345649 A1 | 12/2013 | Stockley, III et al. | |

OTHER PUBLICATIONS

*CookPak®—Self-Heating Packaging Technology for Food*; RCE Technologies; dated Aug. 21, 2013.
*Exothermic Nanocomposite for Self-Contained Ration Heater*; U.S Army NSRDEC—NNI Scientific Accomplishments; dated 2009.
"U.S. Market for Packaging Barrier Resins to Reach 8.6 Billion Pounds by 2009" [online] [retrieved Mar. 17, 2015]. Retrieved from the internet: <URL: http://www.ien.com/article/us-market-packaging/8562>. 6 pages.
Notice of Allowance for U.S. Appl. No. 14/182,034 dated Feb. 17, 2015.
International Search Report and Written Opinion from corresponding International Patent Application No. PCT/US2015/016024 dated Aug. 5, 2015.

\* cited by examiner

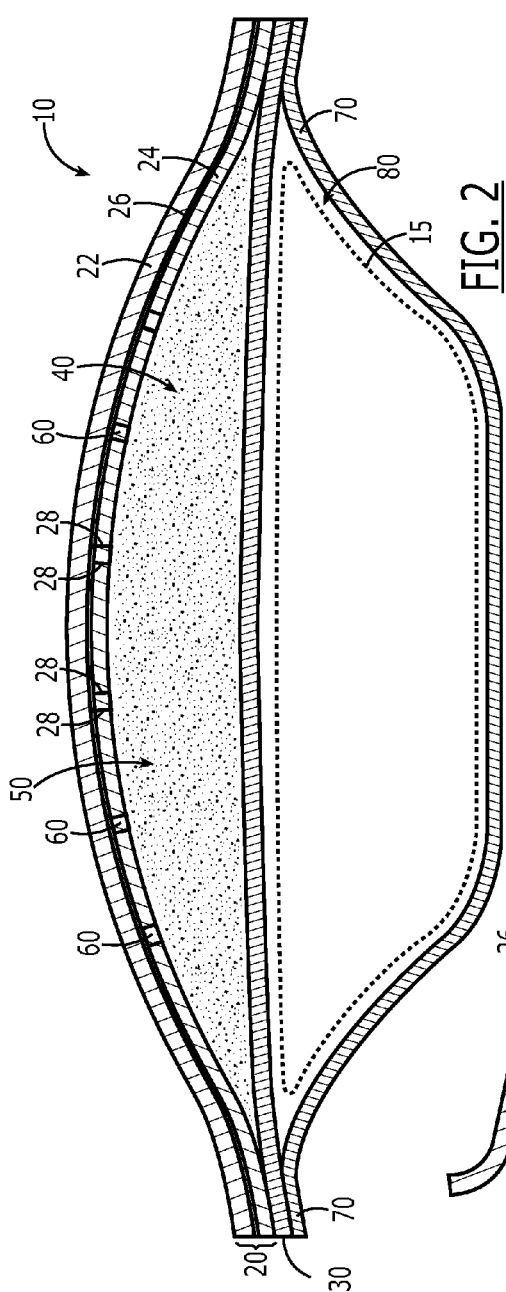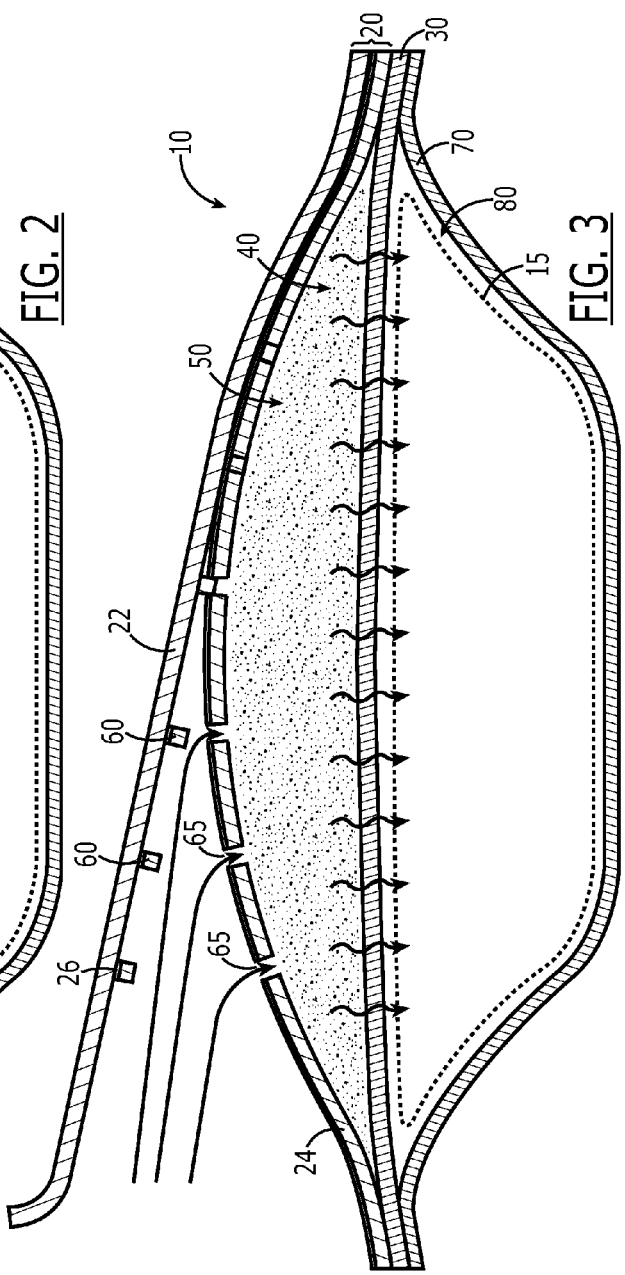

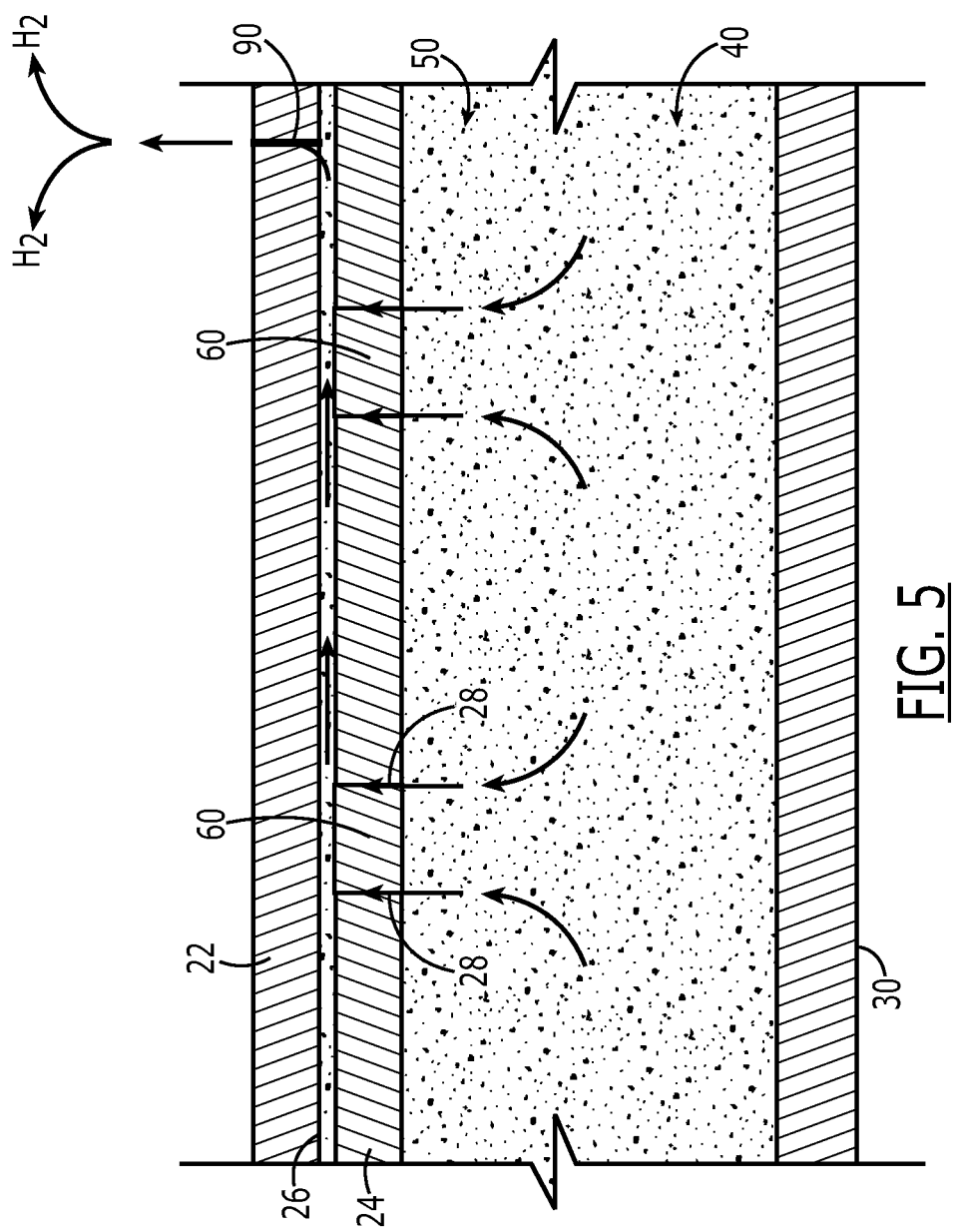

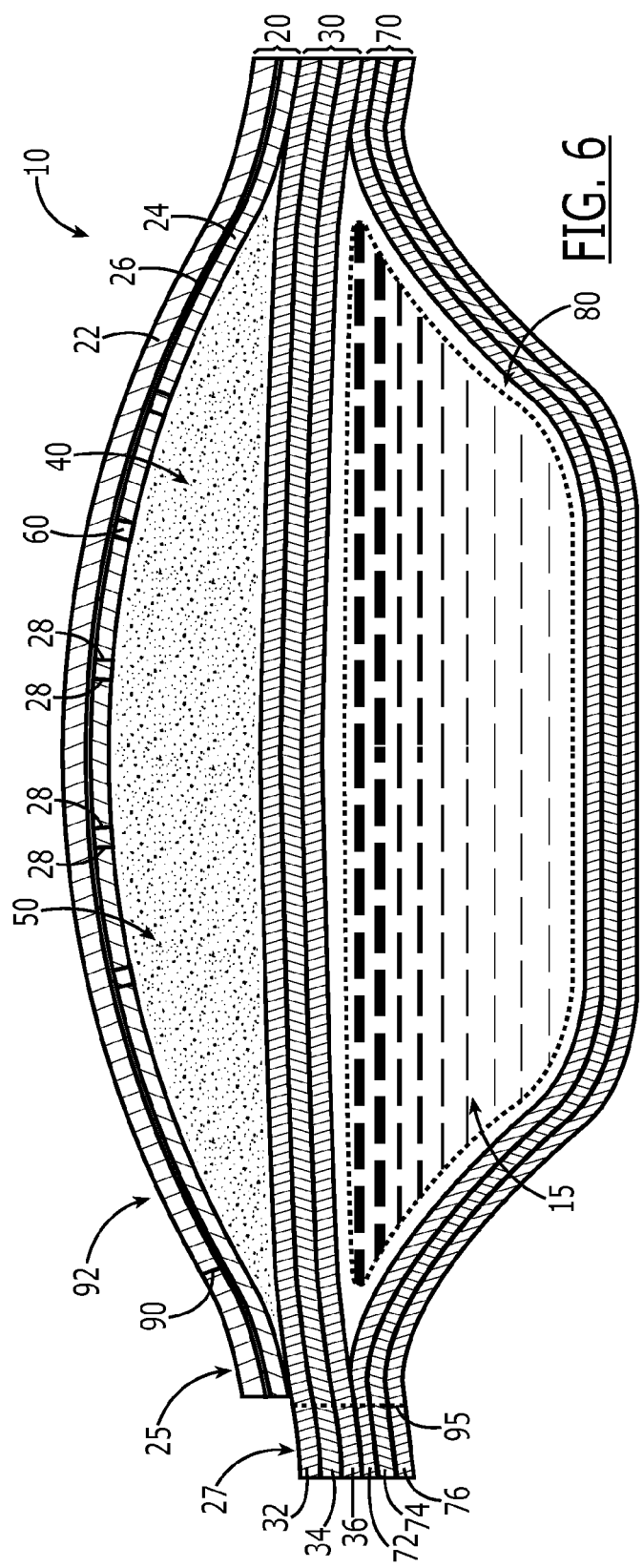

CONTAINER HAVING SELF-CONTAINED HEATER MATERIAL

CROSS-REFERENCE TO RELATED APPLICATIONS

This application claims the benefit of U.S. application Ser. No. 14/182,034 entitled "Container Having Self-Contained Heater Material," filed Feb. 17, 2014, the contents of which are incorporated herein in their entirety.

BACKGROUND

The present disclosure relates to containers with self-contained heating capability, such as for heating contents of the container prior to consumption.

Products such as Meals-Ready-to-Eat (MREs), other food products, medical supplies, and cosmetics often require, or are enhanced by, the application of some heat to the product, such as to allow the product to be consumed properly or, at the very least, to allow for a more pleasant consumer experience. At the same time, consumers don't always have access to heating appliances, such as stoves, ovens, and microwave ovens. Campers in the wilderness, soldiers and military personnel in the field, and others who are removed from modern conveniences, for example, may have a need to use pre-packaged products that require heating, but may have difficulty finding a way to quickly and effectively heat such products.

BRIEF SUMMARY

Accordingly, embodiments of the present invention are directed to containers with built-in heaters that can operate in the absence of any external source of energy. Some embodiments are designed to be pre-filled with product to be heated on demand. As described in greater detail below, the containers are configured to maintain the effectiveness of the heater material and prolong its shelf-life, while at the same time providing the consumer with an easy and efficient way to apply heat to the product stored in the container.

A container is therefore provided for heating items, such as contents stored within the container. In some embodiments, the container includes a first web comprising a laminate of a first film layer and a second film layer, wherein the first film layer is adhered via an adhesive layer to the second film layer. The container may also include a second web disposed adjacent the second film layer of the first web and sealed to the first web so as to form a compartment therebetween, and may further include an air-activated material disposed within the compartment. At least a portion of the first film layer of the first web may be configured to be separated from the second film layer to reveal a plurality of openings in the first film layer so as to allow air to enter the compartment. The air-activated material may be configured to react with the air entering the compartment via the openings to activate the material. Prior to separation of the second film layer from the first film layer, the container may be configured to allow ingress of oxygen into the compartment at a rate less than approximately 3 cc per 100 in$^2$ per 24 hrs. at 23° C.

In some cases, the container may also be configured to allow egress of hydrogen from the container at rate of at least approximately 10 cc per 100 in$^2$ per 24 hrs. at 23° C. Additionally or alternatively, the container may be configured to allow ingress or egress of water vapor into or out of the compartment at a rate of less than approximately 0.030 g per 100 in$^2$ per 24 hrs. at 38° C.

In some embodiments, the second film layer of the first web may comprise a plurality of score lines defining plugs, wherein the plugs are configured to be separated and displaced from the second film layer upon separation of the respective portion of the first film layer to create the openings in the second film layer. The first film layer of the first web may, in some cases, comprise at least one score line defining at least one peelable portion of the first film layer that is configured to be separated from the second film layer, and the at least one score line of the first film layer, the adhesive layer, and the score lines of the second film layer may define a plurality of tortuous paths through a thickness of the first web configured to allow hydrogen gas to escape from the compartment.

In other embodiments, the first film layer of the first web may define the openings, and the second film layer may be configured to cover the openings when the second film layer is adhered to the first film layer.

According to other embodiments, a container may be provided for heating items, where the container includes a first web comprising a laminate of a first film layer and a second film layer, and wherein the first film layer is adhered via an adhesive layer to the second film layer. The container may also include a second web disposed adjacent the second film layer of the first web and sealed to the first web so as to form a compartment therebetween, and may further include an air-activated material disposed within the compartment. At least a portion of the first film layer of the first web may be configured to be separated from the second film layer to reveal a plurality of openings in the first film layer so as to allow air to enter the compartment. The air-activated material may be configured to react with the air entering the compartment via the openings to activate the material. Prior to separation of the second film layer from the first film layer, the container may be configured to allow egress of hydrogen from the container at rate of at least approximately 10 cc per 100 in$^2$ per 24 hrs. at 23° C.

In some cases, the container may be configured to allow ingress of oxygen into the compartment at a rate less than approximately 3 cc per 100 in$^2$ per 24 hrs. at 23° C. Additionally or alternatively, the container may be configured to allow ingress or egress of water vapor into or out of the compartment at a rate of less than approximately 0.030 g per 100 in$^2$ per 24 hrs. at 38° C.

In some embodiments, the second film layer of the first web may comprise a plurality of score lines defining plugs, wherein the plugs are configured to be separated and displaced from the second film layer upon separation of the respective portion of the first film layer to create the openings in the second film layer. The first film layer of the first web may, in some cases, comprise at least one score line defining at least one peelable portion of the first film layer that is configured to be separated from the second film layer, and the at least one score line of the first film layer, the adhesive layer, and the score lines of the second film layer may define a plurality of tortuous paths through a thickness of the first web configured to allow hydrogen gas to escape from the compartment.

In other embodiments, the first film layer of the first web may define the openings, and the second film layer may be configured to cover the openings when the second film layer is adhered to the first film layer.

According to still other embodiments, a container may be provided for heating items, where the container includes a first web comprising a laminate of a first film layer and a second film layer, and wherein the first film layer is adhered via an adhesive layer to the second film layer. The container may also include a second web disposed adjacent the second film layer of the first web and sealed to the first web so as to form a compartment therebetween, and may further include an air-activated material disposed within the compartment. At least a portion of the first film layer of the first web may be configured to be separated from the second film layer to reveal a plurality of openings in the first film layer so as to allow air to enter the compartment. The air-activated material may be configured to react with the air entering the compartment via the openings to activate the material. Prior to separation of the second film layer from the first film layer, the container may be configured to allow ingress or egress of water vapor into or out of the compartment at a rate of less than approximately 0.030 g per 100 in$^2$ per 24 hrs. at 38° C.

In some cases, the container may be configured to allow ingress of oxygen into the compartment at a rate less than approximately 3 cc per 100 in$^2$ per 24 hrs. at 23° C. Additionally or alternatively, the container may be configured to allow egress of hydrogen from the container at rate of at least approximately 10 cc per 100 in$^2$ per 24 hrs. at 23° C.

In some embodiments, the second film layer of the first web may comprise a plurality of score lines defining plugs, wherein the plugs are configured to be separated and displaced from the second film layer upon separation of the respective portion of the first film layer to create the openings in the second film layer. The first film layer of the first web may, in some cases, comprise at least one score line defining at least one peelable portion of the first film layer that is configured to be separated from the second film layer, and the at least one score line of the first film layer, the adhesive layer, and the score lines of the second film layer may define a plurality of tortuous paths through a thickness of the first web configured to allow hydrogen gas to escape from the compartment.

In other embodiments, the first film layer of the first web may define the openings, and the second film layer may be configured to cover the openings when the second film layer is adhered to the first film layer.

BRIEF DESCRIPTION OF THE SEVERAL VIEWS OF THE DRAWING(S)

Having thus described the disclosure in general terms, reference will now be made to the accompanying drawings, which are not necessarily drawn to scale, and wherein:

FIG. 2 is a cross-sectional view of the container of FIG. 1 prior to peeling away of the first film layer in accordance with an embodiment of the invention;

FIG. 3 is a cross-sectional view of the container of FIG. 1 after peeling away of the first film layer in accordance with an embodiment of the invention;

FIG. 5 is a partial cross-sectional view along line 5-5 in FIG. 4; and

FIG. 6 is a representation of a cross-sectional view along line 6-6 in FIG. 4.

DETAILED DESCRIPTION OF THE DRAWINGS

The present invention now will be described more fully hereinafter with reference to the accompanying drawings in which some but not all embodiments of the inventions are shown. Indeed, these inventions may be embodied in many different forms and should not be construed as limited to the embodiments set forth herein; rather, these embodiments are provided so that this disclosure will satisfy applicable legal requirements Like numbers refer to like elements throughout.

Conventional packages and containers with self-contained heating elements rely on an exothermic reaction that takes place when a zinc-based heating material is placed in an electrolyte solution. The zinc material uses oxygen as a cathode and zinc as the anode. Thus, when the zinc material comes into contact with oxygen from the air, zinc is converted to zinc oxide and heat is released, which can be used to heat any of various items, such as the contents of the package.

Because there is a limited amount of zinc in the air-activated material, once the zinc has been fully consumed (e.g., once all of the zinc has been converted to zinc oxide), the exothermic reaction stops, and no more heat is available (e.g., for warming the contents of the package). As such, any premature reaction of the air-activated material with air, such as while the package is being stored and prior to use of the enclosed product by the consumer, reduces the heating capacity of the heater when the user finally activates it and also decreases the shelf-life of the container and/or its contents. Some conventional containers, for example, use four layers of 3-mil-thick polyethylene that serve as an adequate moisture barrier to maintain the moisture level of the heater material; however, such layers may be inadequate as an oxygen barrier. Moreover, some conventional containers for holding air-activated material may have other openings and passages that allow air to enter and react with the air-activated material, further compromising the effectiveness and shelf-life of the container.

Figure 1:
FIG. 1 illustrates a container in accordance with one embodiment of the invention.

Accordingly, embodiments of a container that includes self-contained heater material are described that provide improved barrier functionality with respect to the premature ingress of air and egress of water and a lower cost as compared to conventional containers. A container 10, such as a container for heating contents (e.g., a ration of food), in accordance with one embodiment of the invention is depicted in FIGS. 1-3. As shown in FIG. 2, the container 10 may comprise a first web 20, a second web 30 sealed to the first web so as to form a compartment 40 therebetween, and an air-activated material 50 disposed within the compartment. In some embodiments, as depicted, the first web 20 may comprise a laminate of a first film layer 22 and a second film layer 24. For example, the first film layer 22 may be adhered to the second film layer 24 using an adhesive layer 26, which may be, for example, a pressure-sensitive adhesive.

According to embodiments of the present invention, the second film layer 24 of the first web 20 may comprise a plurality of score lines 28 defining plugs 60 of material. For example, the second film layer 24 may be precision scored (e.g., die cut) to define plugs 60; however, the plugs 60 may be maintained within the second film layer 24 so as to avoid creating holes in the second film layer where air may prematurely enter the compartment 40 and react with the air-activated material 50 held within. The first web 20 may thus act as a barrier against the ingress of air into and the egress of water vapor out of the compartment 40, both by virtue of the material selected for the layers 22, 24 of the first web and as a result of the substantial structural continuity of the material that is achieved via the plugs 60. In some cases, the second film layer 24 of the first web 20 may also have a high barrier layer, such as metalized oriented polypropylene film, that keeps moisture in the compartment 40 and keeps air out.

With reference to FIG. 3, at least a portion of the first film layer 22 of the first web 20 (e.g., the entire first film layer as depicted in FIG. 3) may be configured to be peeled away from the second film layer 24. For example, a pull tab (such as the pull tab 29 shown in FIG. 4, for example) or other portion of the first film layer 22 may be provided that is not laminated to the second film layer 24 (e.g., an area where there is no adhesion between the first and second film layers), such that a user can grasp the pull tab and pull the first film layer 22 away from the second film layer 24, separating the two layers at the interface formed by the adhesive 26. For example, the pull tab can be formed by providing an adhesive-free "knock-out" region in the interface between the first and second films 22, 24 of the first web 20 that is bounded by an edge of the first web or score lines that go through at least the first film layer (as shown, for example, by score lines 90 in FIG. 4). In some cases, for example, precision scoring the second film layer 24 may involve cutting a score line (e.g., using mechanical or laser die cutting techniques) through the second film layer only, such that the score lines 28 shown in FIG. 2 do not go through the adhesive layer 26.

The plugs 60 may be configured to be separated and displaced from the second film layer 24 upon peeling away of the respective portion of the first film layer 22 to create openings 65 in the second film layer 24. In other words, as the first film layer 22 is pulled or peeled away from the second film layer 24, the plugs 60 are separated from the rest of the second film layer 24 along the pre-defined score lines 28 and leave behind the openings 65, which are now (as a result of the peeling away of the first film layer 22) exposed to the ambient environment. The openings 65, in turn, allow oxygen (e.g., air) to enter into the compartment 40 and react with the air-activated material 50 and activate the material, for example, starting an exothermic reaction that produces heat (e.g., to heat the contents 15 of the container).

With continued reference to FIGS. 2 and 3, the container 10 may further comprise a third web 70 attached to the second web 30 to form a holding space 80 therebetween, where the contents to be heated 15 are received within the holding space. The container 10 may be configured (e.g., sized and shaped) such that the holding space 80 can hold various types of products, from food products (e.g., meals, soups, sauces, chocolate syrup, infant formula, etc.) to medical products (e.g., lotions, ointments, compresses, splints, etc.) to cosmetic products, and so on.

In addition to the size and/or shape of the container 10, the materials forming the first, second, and third webs 20, 30, 70 may be selected to impart various properties to the container that may allow for better storage of the particular contents (e.g., by improving the shelf-life of the contents or preserving freshness, taste, appearance, texture, etc. of the product), easier access to or delivery of the contents stored therein, and/or a better consumption experience (e.g., by providing for the contents to be heated more evenly, more thoroughly, or to a particular temperature or range of temperatures). Moreover, as noted above, the material of the first and second webs 20, 30 forming the compartment 40 in which the air-activated material is held may be selected to increase the shelf-life of the heater material itself, thereby prolonging the usability of the container. According to some embodiments, the shelf-life of the air-activated material may be increased by the material selection and design of the container 10 as described herein to a shelf-life of 8 months, 9 months, 10 months, 11 months, 12 months, or more.

For example, in some embodiments, the first film layer 22 of the first web 20 may comprise or consist of poly(ethylene terephthalate) (PET) or other polymer material with appropriate oxygen and moisture barrier properties. Furthermore, in some embodiments, the second film layer 24 of the first web 20 may comprise or consist of metalized oriented polypropylene (mOPP) or other metalized films to further provide a barrier with respect to the passage of light, moisture, and oxygen, while at the same time providing adequate toughness and allowing the layers to be heat sealed to other layers and webs to form the container, as described in greater detail below. In some cases, the metalized material of the second film layer 24 may further serve as a heat shield to allow the exothermic reaction occurring at the air-activated material 50 to more efficiently heat the contents 15 (e.g., by directing the heat towards the contents and reducing the amount of heat that is lost to the ambient environment).

In some cases, the third web 70 may comprise multiple film layers, as well. For example, the third web 70 may comprise or consist of a layer of PET laminated to a layer of mOPP, such that the third web can be heat sealed to the first web 20 and/or the second web 30 to provide an enclosed holding space 80. At the same time, the presence of the metalized film can act as a heat shield as described above to direct the heat from the air-activated material 50 that may otherwise have a tendency to escape from the container (e.g., passing through the holding space 80 and out the other side) to be re-directed back to the holding space to heat the contents 15. In some embodiments, the layer of PET may be disposed closest to the holding space 80, with the layer of mOPP being disposed on an outer surface of the PET layer.

Although certain materials are described above for forming the first and second film layers 22, 24 of the first web 20, other materials may be used as appropriate for providing the same or similar oxygen and moisture barrier properties to the container. Moreover, in some cases, a further coating or layer may be applied to the outer surface of the first web 20, adjacent the first film layer 22, which may serve as an additional oxygen barrier. For example, the first web 20 may, in some embodiments, comprise a third film layer (not shown) disposed adjacent the first film layer 22, where the third film layer comprises an oxygen barrier. In addition, other materials, layers, pigments, etc. may be added to the structure of the first web 20 to enhance the appearance, manufacturability, or barrier properties of the first web.

For example, in one embodiment, the first web 20 may have a structure as follows (in the direction from the outer surface of the first web towards the compartment 40): 92 ga PET/ink/PSA/118 ga mOPP. The second web 20, as an example, may have a structure as follows (in the direction from the compartment 40 towards the holding space 80): oriented polypropylene (OPP)/ink/adhesive/118 ga mOPP. Additionally or alternatively, the third web 70, in some embodiments, may have a structure as follows (in the direction from the holding space 80 towards the outer surface of the third web): 92 ga PET/ink/adhesive/118 ga mOPP.

Embodiments of the container 10 as described above, in addition to providing for increased shelf-life of the air-activated material 50, may also reduce the thickness of the packaging and weight of the empty container (prior to insertion of the heater material and/or contents), thereby reducing the manufacturing costs. For example, many conventional containers for holding comparable products may typically use three webs to hold the air-activated material and may, as a result, have a thickness of approximately 334 microns and weigh approximately 8-9 grams. In contrast, embodiments of the invention as described above are configured to form a compartment 40 using only two webs 20, 30 and may thus have a thickness of approximately 113 microns and weigh approximately 3-5 grams, such as 4 grams.

In some embodiments, a vacuum may be pulled between the second and third webs 30, 70 to bring the contents 15 of the holding space 80 into closer contact with the heater material 50 of the compartment 40. For example, when the contents 15 are products that are solid in form (such as, for example, a thermoplastic splint), removing the air in the holding space 80 via a vacuum may thus allow the heat emitted from the heater material 50 to more effectively be transferred to the contents (e.g., via conduction as well as via radiation).

Figure 4:
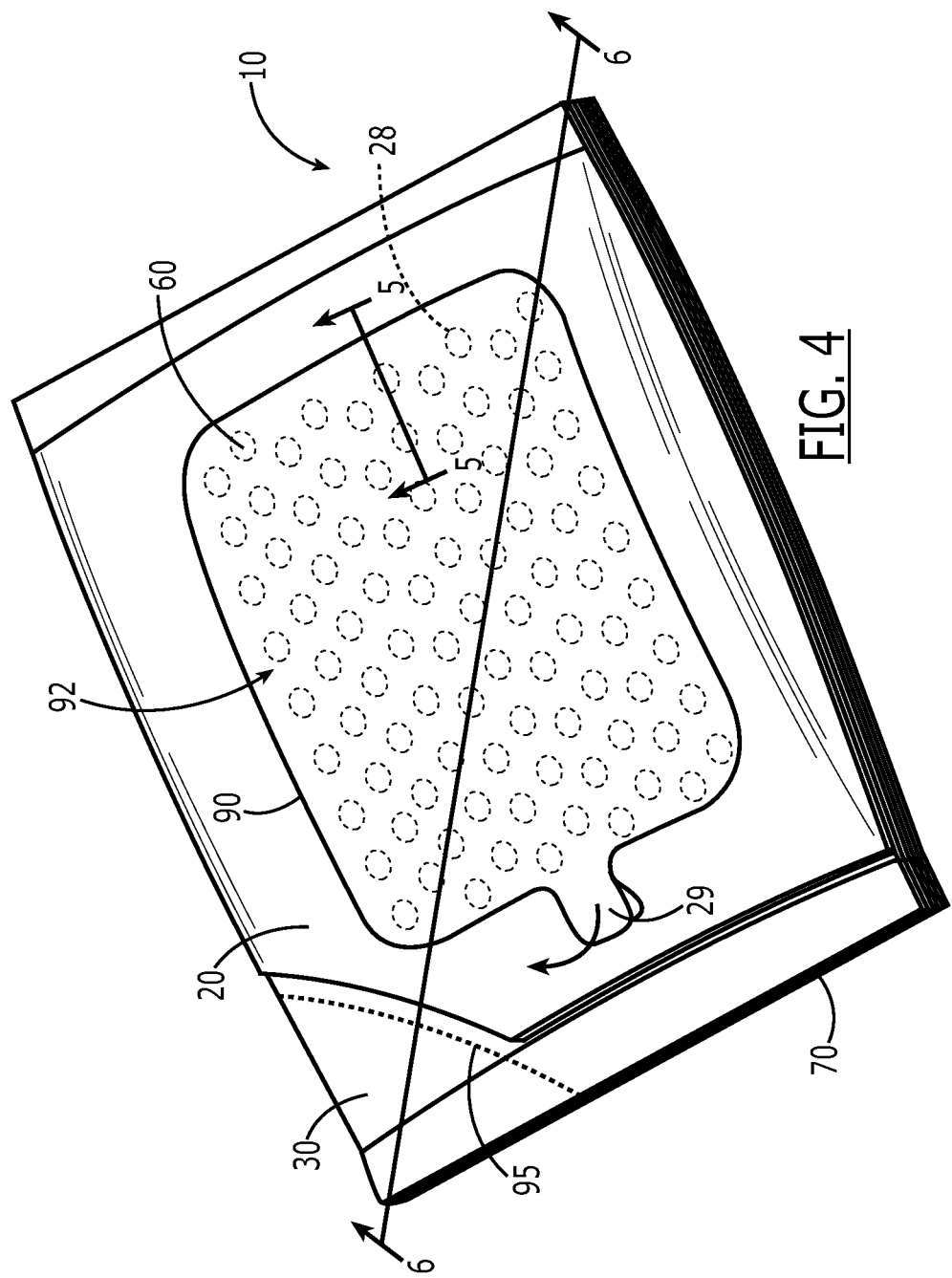
FIG. 4 is a perspective view of a container in accordance with an embodiment of the invention.

As noted above, the container 10 may be configured to facilitate the formation of different types of containers for holding different types of contents 15. In some embodiments, for example, the container 10 may be configured to hold a lotion, ointment, or other liquid or gel-like product. With reference to FIGS. 4 and 6, for example, in some embodiments both of the second and third webs 30, 70 may comprise multiple film layers laminated together. For example, one or both of the second and third webs 30, 70 may comprise a layer of metal foil laminated between two layers of cast polypropylene. In FIG. 6, for example, the second web 30 includes a first film layer 32 of cast polypropylene laminated (e.g., adhered via adhesive) to a second film layer 34 of metal foil, which is in turn laminated to a third film layer 36 of cast polypropylene. Likewise, the third web 70 includes a first film layer 72 of cast polypropylene laminated (e.g., adhered via adhesive) to a second film layer 74 of metal foil, which is in turn laminated to a third film layer 76 of cast polypropylene. The metal foil may be, for example, aluminum foil. In some cases, instead of only one film layer of metal foil, multiple film layers of metal foil may be laminated between the cast polypropylene in one or both the second and third webs 30, 70 to increase the effectiveness of the heat shield, such as two or three layers of metal foil or more.

As described above with respect to metalized films, the metal foil layers may reduce the amount of heat that escapes from the container 10 to the external environment by acting as heat shields on both sides of the holding space 80 that redirect the heat back toward the contents 15 held within the holding space 80. In addition, the cast polypropylene layers may allow the second and third webs 30, 70 to be heat sealed to each other, as well as to the first web 20 (which, as described above, may include a first film layer 22 of PET). In this way, a container may be formed that includes a seal around 4 sides of the packaging. Moreover, the compatibility of cast polypropylene with the PET/mOPP laminate may allow the first web 20 to be heat sealed directly to the second web 30, which may help reduce the cost of manufacturing the container.

With continued reference to FIGS. 4 and 6, in some cases, the first film layer 22 of the first web 20 may comprise at least one score line 90 defining at least one peelable portion 92 of the first film layer that is configured to be peeled away from the second film layer 24. The peelable portion 92 may include, for example, a pull tab 29 that can be grasped by the user and used to peel the peelable portion away from the container 10 to create the openings 65 (shown in FIG. 3) in the second film layer 24 of the first web 20 (via the score lines 28) that allow air to enter into the compartment 40. The peelable portion 92 may be configured (e.g., sized and shaped) and arranged with respect to the surface of the container 10 such that when the openings 65 are created via removal of the peelable portion, the openings allow air to contact the air-activated material 50 in the compartment 40 in an even and controlled manner, such that the exothermic reaction that results applies heat to the contents 15 in an efficient manner.

Accordingly, although a single peelable portion 92 centrally disposed on a majority of the surface of the container 10 is shown in FIG. 4, in some embodiments, more than one peelable portion may be provided, and the peelable portions may be arranged in different ways to accommodate the amount and orientation of the heater material 50. In such a case, the peelable portions may be independently peelable, such that a degree of heating (e.g., heating of the contents 15) may be controlled by the user by controlling the amount of air that is allowed to contact the heater material 50. For example, where three peelable portions are provided (not shown), the user may be able to produce heat at a "low" level by removing only one of the peelable portions. The user may similarly be able to produce heat at a "medium" level by removing two of the peelable portions, and the user may likewise produce heat at a "high" degree by removing all three of the peelable portions and allowing the maximum amount of air to enter into the compartment 40 and react with the heater material 50.

In still other embodiments, one or more of the peelable portion(s) 92 may be configured such that the first film layer 22 can be re-adhered to the second film layer 24 via the adhesive layer 26, such that the compartment 40 is re-sealable. As an example, at least a portion of the first film layer 22 of the first web 20 may be configured to be re-adhered to the second film layer 24 via the adhesive layer 26 so as to re-engage the plugs 60 within the corresponding openings 65 in the second film layer, changing the configuration of the film layers from that shown in FIG. 3 to that shown in FIG. 2. In so doing, no additional oxygen may be introduced to the compartment 50, allowing any unreacted heating material (once the oxygen in the compartment is consumed) to remain unreacted until such time that the first film layer 22 is again peeled away from the second film layer 24 and additional oxygen is introduced into the compartment 40 via the openings 65 to re-start the reaction of the heating material.

Moreover, the container 10 may include other features to assist the user in consuming or accessing contents 15. In the example of a container 10 for holding lotion that is heated before application, the size of the first web 20 may be smaller than that of the second and third webs 30, 70, such that the region 25 (shown in FIG. 6) in which the first web is sealed to the second web is different from the region 27 in which the second web is sealed to the third web. In addition, a line of weakness 95 may be provided between the two seal regions 25, 27, where the line of weakness is configured to allow a user to tear the second and third webs 30, 70 to be able to dispense the contents 15 from the holding space 80 of the container 10. The line of weakness may, for example, comprise perforations that form a tear strip to facilitate removal of a portion of the container to create an outlet from which the contents 15 may be dispensed. In other cases, however (not shown), the container 10 may further include nozzles, spouts, and other pre-defined outlets via which the contents 15 may be dispensed.

Turning now to FIG. 5, in some embodiments the at least one score line 90 of the first film layer 22, the adhesive layer 26, and the score lines 28 of the second film layer 24 may define a plurality of tortuous paths through a thickness of the first web 20 that are configured to allow hydrogen gas to escape from the compartment 40. For example, in some cases, hydrogen gas may be produced as a byproduct of corrosion of the zinc in the heater material 50 while it is being stored in the compartment 40 (e.g., prior to peeling away of the first web 20 or a portion of the first web to purposely initiate the exothermic reaction). In such cases, the hydrogen gas may accumulate in the compartment 40 and may cause the container 10 to bulge with excess pressure in the compartment. This may cause the container 10 to be unsightly or may cause a consumer to shy away from purchasing a container, as the consumer may have the impression that the container is defective, damaged, or nearing the end of its shelf-life, which may not be the case.

By providing score lines 28 in the second film layer 24, any hydrogen gas that is released within the compartment 40 (represented by arrows in FIG. 5) may be able to travel through the second film layer 24 via the score lines. The hydrogen gas may diffuse through the adhesive layer 26, and may continue towards release to the external environment by travelling through the score line 90 of the first film layer 22, as illustrated. The score lines 28, 90 may, for example, be in the range of approximately 5-7 microns wide, and the hydrogen gas may be able to pass through due to the small size of the hydrogen molecule. In some cases, diffusion through the adhesive layer 26 may be facilitated by pattern applying a channel in the adhesive layer to provide a pathway for the hydrogen to travel from the score lines 28 of the second film layer 24 to the score lines 90 of the first film layer 22. In this way, hydrogen may be allowed to exit the compartment 40 without compromising the integrity of the first web 20, such that the first web is still capable of acting as a barrier against the entry of air into the compartment and the exit of moisture from the compartment to the environment. In other cases where score lines 90 are not provided in the first film layer 22 of the first web 20, the hydrogen may, in some cases be allowed to exit the compartment 40 via the free lateral edges of the first and second webs 20, 30 (e.g., travelling through the score lines 28 of the second film layer 24 and laterally out from the container's side edges via the adhesive layer).

The diffusion of hydrogen through the first web 20 may, in some cases, be regulated based on the available pathways for diffusion. Thus, in some embodiments, at least one score line may be defined in one of the first film layer 22 of the first web 20 or the second film layer 24 of the first web, where the at least one score line is configured (e.g., via the length, depth, thickness, and/or shape) to allow a regulated amount of hydrogen gas to escape from the compartment. For example, the amount of hydrogen gas that is to be diffused (and/or desired rate of diffusion) may be calculated (e.g., based on the particular composition of the material 50 in the compartment 40, etc.), and the total lineal amount of scoring in the second film layer 24 and/or in the first film layer 22 of the first web 20 that is needed to allow for the calculated diffusion may, in turn, be calculated. In some cases in which the total amount of scoring provided by the score lines 28, 90 is less than the desired total lineal amount of scoring (e.g., the calculated amount), additional score lines may be provided in the first and/or second film layers 22, 24 to increase the amount of diffusion and/or adjust the rate at which the diffusion can occur. The additional scoring may be in the form of lines, curves, and/or enclosed shapes, but may be provided for the sole purpose of diffusing hydrogen, rather than for forming the plugs 60 for allowing the ingress of air into the compartment 40 or for providing the peelable portion(s) 92 shown in FIG. 4.

Embodiments of a method for making a container, such as a container 10 as described above for heating contents stored therein, are also provided. In some embodiments, the method may include laminating a first film layer to a second film layer to form a first web, where the first film layer is adhered via an adhesive layer to the second film layer, and where the second film layer comprises a plurality of score lines defining plugs. The score lines in the second film layer of the first web can be formed by using a laser to ablate material of the second film layer. The laser may be tuned such that it has the appropriate power density to ablate through the thickness of the second film layer without penetrating through the first film layer of the first web and/or without penetrating the adhesive layer between the first and second film layers. Alternatively, the score lines may be mechanically formed, such as by die-cutting.

A second web may be disposed adjacent the second film layer of the first web, and the first web may be sealed to the second web so as to form a compartment between the first and second webs, as described above. An air-activated material may be disposed within the compartment. Furthermore, a third web may be attached to the second web to form a holding space between the second and third webs. In some cases, an air-activated material as described above may be disposed within the compartment, and the container may be provided for downstream handling (such as to place contents into the holding space) with the air-activated material already present in the container. In other cases, however, the container may be provided without the air-activated material, such as on a roll of empty containers, and the air-activated material and the contents may be placed in the appropriate positions within the container at the time of packaging.

As described above, the first web may act as a barrier against the ingress of air into the compartment, and at least a portion of the first film layer of the first web may be configured to be peeled away from the second film layer. The plugs, in turn, may be configured to be separated and displaced from the second film layer upon peeling away of the respective portion of the first film layer so as to create openings in the second film layer that allow air to enter the compartment. The air-activated material is configured to react with oxygen from the air entering the compartment via the openings to activate the material, such that the contents of the container, for example, may be heated as a result of an exothermic reaction as described above and illustrated in the accompanying figures.

In some cases, the first film layer of the first web may comprise at least one score line defining at least one peelable portion of the first film layer that is configured to be peeled away from the second film layer. As described above, the at least one score line of the first film layer, the adhesive layer, and the score lines of the second film layer may define a plurality of tortuous paths through a thickness of the first web configured to allow hydrogen gas to escape from the compartment. In some embodiments, additional score lines may be provided in the first and/or second film layers to adjust and/or control the amount and/or rate of diffusion of the hydrogen gas through the first web.

The first film layer of the first web may comprise poly (ethylene terephthalate) in some embodiments, and the second film layer of the first web may comprise metalized oriented polypropylene. In some cases, the second web may comprise a layer of oriented polypropylene laminated to a layer of metalized oriented polypropylene. In other cases, the second web and the third web may each comprise a layer of metal foil laminated between two layers of cast polypropylene.

As described above, embodiments of the container are configured to meet certain performance and manufacturing requirements and preferences. For example, embodiments of the container should be designed to limit the ingress of oxygen into the compartment holding the air-activated material to avoid significant unintended reaction of the heating material. Moreover, the production or accumulation of hydrogen within the compartment (e.g., as a result of the reaction of the zinc anode with water present in the container) should be allowed to vent out of the compartment to avoid swelling of the compartment or bursting of the container.

The accumulation of hydrogen in the compartment depends to some extent on the combined hydrogen transmission rate of the first and second webs. As a result, hydrogen can accumulate in the compartment when the hydrogen generation rate is greater than the average hydrogen transmission rate of the container.

In general, the direction of water vapor transfer (e.g., into or out of the compartment) depends on the combined water vapor transmission rate of the first and second webs, the relative humidity of the environment, and the relative humidity of the electrolyte solution. The net transmission of water vapor typically occurs in a direction from a location of higher relative humidity to a location of lower relative humidity. Thus, when the container is in a relatively humid environment and a first web, for example, is selected that has a high water vapor transfer rate, the net transfer of water vapor is into the compartment, and water vapor can quickly accumulate and cause the compartment (and the container) to swell, which is unsightly and may be destructive to the container and/or its contents. At the same time, if the container is in a relatively low humidity environment and materials for the first and second webs are selected that collectively provide a high water vapor transfer rate, water vapor can pass out of the compartment, and the electrolyte solution may be at risk of dehydrating, which again may have negative effects on the container and the functionality of the heating material.

The actual oxygen, hydrogen, and water vapor transmission rates for a particular container may depend on several factors, including the materials chosen for the different film layers of the different webs, the thicknesses of the films, and the pattern of tortuous paths through the thickness of the first web, and the particular construction of the container, among other things. In addition to these factors, the water vapor transmission rate may also depend on the relative humidity of the electrolyte solution as compared to that of the environment, as described above. At the same time, the materials selected for a particular container should be suitable for the particular manufacturing processes involved in making the container. For example, in some applications, the materials (in addition to exhibiting appropriate oxygen, hydrogen, and water vapor transmission rates as described above) must also withstand the temperatures required for heat sealing and assembling the container, which may range from approximately 170° F. to approximately 200° F.

The inventors have tested various configurations of containers according to the embodiments described above to determine the particular hydrogen, oxygen, and water vapor transmission rates under different scenarios.

In one comparative example test case, the air-activated heating material included zinc, carbon, polytetrafluoroethylene (PTFE), and water. The electrolyte solution was 28.5% potassium bromide (KBr) with a relative humidity of around 85%. The first and second webs 20, 30 each had a nominal thickness of 3.5 mils (0.0035 in), and each web comprised inner and outer layers of a linear low-density polyethylene (LLDPE) with a middle layer of ethylene-vinyl alcohol (EVOH) nylon coextrusion. In this example, an air diffuser layer (not shown) comprising a felt sheet was placed against an inner surface of the first web 20 to create a tortuous path for the oxygen on the outside of the package to enter into the compartment 40 and react with the air-activated material 50. Moreover, a wicking layer (not shown) comprising a sheet of a hydroentangled nonwoven blend of 55% cellulose and 45% polyester (e.g., BlueSorb® 750 wiper sheet) was placed on an inner surface of the wicking layer to serve as a distribution medium for the electrolyte. The published oxygen transmission rate of each web was <0.3 cc per 100 in$^2$ per 24 hrs. (at 73° F. and 80% relative humidity), and the published water vapor transmission rate of each web was <0.5 g per in$^2$ per 24 hrs. (at 100° F. and 90% relative humidity).

When this heating material and web construction were tested in a container placed in a 100% oxygen environment (100% $\Delta O_2$) pressurized to 5 psi gauge pressure (hyperbaric oxygen tank), the observed incoming oxygen transmission rate, corrected to atmospheric pressure, was 4+/−1.5 cc per 100 in$^2$ per 24 hrs. at 23° C. The observed outgoing hydrogen transmission rate of the first web was approximately 10 cc per 100 in$^2$ per 24 hrs. at 23° C. in a 100% hydrogen environment (100% $\Delta H_2$). Further, the observed water vapor transmission rate was 0.030+/−0.005 g per 100 in$^2$ per 24 hrs. at 38° C. and a relative humidity of 90% external to the test package (90% $\Delta RH$).

Another comparative example employed the same air-activated heating material, but a different web construction and electrolyte. As in the test case described above, the first and second webs 20, 30 in this scenario comprised inner and outer layers of LLDPE with a middle layer of EVOH nylon coextrusion and had a nominal thickness of 3.5 mils (0.0035 in). The published oxygen transmission rate of each web was <0.3 cc per 100 in$^2$ per 24 hrs. (at 73° F. and 80% relative humidity), and the published water vapor transmission rate of each film layer was <0.5 g per in$^2$ per 24 hrs. (at 100° F. and 90% relative humidity). In addition, however, the first film layer 22 of the first web 20 comprised a barrier polyester material with a peelable, aluminum oxide sealant. As in the previous example, an air diffuser layer (not shown) was placed on an inner surface of the first web 20. The barrier polyester of the first film layer 22 had a nominal thickness of 2.5 mils (0.0025 in), a published oxygen transmission rate of 0.05 cc per 100 in$^2$ per 24 hrs., and a published water vapor transmission rate of 0.05 g per 100 in$^2$ per 24 hrs. The electrolyte solution in this case was a 50% potassium hydroxide (KOH) solution with a relative humidity of around 15%.

When this heating material and web construction were tested in a 100% oxygen environment pressurized to 5 psi gauge pressure (hyperbaric oxygen tank), the observed incoming oxygen transmission rate, corrected to atmospheric pressure, was 0.05 cc per 100 in$^2$ per 24 hrs. The observed outgoing hydrogen transmission rate of the web construction was 26.4 cc per 100 in$^2$ per 24 hrs. Further, the observed water vapor transmission rate was 0.0564 g per 100 in$^2$ per 24 hrs. (at 38° C. and a relative humidity of 90% external to the container). In both of the abovementioned comparative examples, one of the preferred vapor transmission rates was not achieved.

In a test example of an embodiment of the invention, the air-activated heating material included zinc, carbon, polytetrafluoroethylene (PTFE), and water. The electrolyte solution was 28.5% potassium bromide (KBr) with a relative humidity of around 85%. The first web 20 had a nominal thickness of 2.0 mils (0.002 in) and included an first (outer) film layer of a poly(ethyelene terephthalate) material having a thickness of 0.120 mils and a second (inner) film layer of metalized oriented polypropylene (mOPP) having a thickness of 0.118 mils. The first web included a series of cut lines (e.g., die cuts) that partially penetrated the web to generate a pattern similar to that shown in FIG. 3. The second web 30 had a nominal thickness of 2.0 mils (0.002 in) and included of a first (outer) film layer of oriented polypropylene (OPP) having a thickness of 0.06 mils and a second (inner) film layer of metalized oriented polypropylene (mOPP) having a thickness of 0.118 mils. In this example, an air diffuser layer (not shown) comprising a felt sheet was placed against an inner surface of the first web 20 to create a tortuous path for the oxygen on the outside of the package to enter into the compartment 40 and react with the air-activated material 50. Moreover, a wicking layer (not shown) comprising a sheet of a hydroentangled nonwoven blend of 55% cellulose and 45% polyester (e.g., BlueSorb® 750 wiper sheet) was placed on an inner surface of the wicking layer to serve as a distribution medium for the electrolyte.

When this heating material and web construction were tested in a 100% oxygen environment pressurized to 5 psi gauge pressure (hyperbaric oxygen tank), the observed incoming oxygen transmission rate, corrected to atmospheric pressure, was 0.50 cc per 100 in$^2$ per 24 hrs. The observed outgoing hydrogen transmission rate of the web construction was 13.9 cc per 100 in$^2$ per 24 hrs. Further, the observed water vapor transmission rate was 0.017 g per 100 in$^2$ per 24 hrs. (at 38° C. and a relative humidity of 90% external to the container).

Such a construction appears to allow for a low oxygen transmission rate into the compartment of the container holding the heating material, a low hydrogen generation rate within the compartment, an adequately high hydrogen transmission rate out of the compartment, and a low water vapor transfer rate (in or out). As a result, hydrogen is permitted to escape through the first web faster than the heating material can oxidize and generate hydrogen, minimizing swelling of the container. Further, the electrolyte solution may be selected to have a relative humidity that is lower than the relative humidity of the container's external environment. This eliminates a net outgoing transfer of water vapor and avoids excessive degradation of the heating material's performance.

As such, the container (e.g., through the material selection and/or configuration of the first and second webs, for example) may be configured to allow ingress of oxygen into the compartment at a rate less than approximately 3 cc per 100 in$^2$ per 24 hrs. at 23° C., 0% ΔRH, and 100% ΔO$_2$. Also, the container may be configured to allow egress of hydrogen from the container at rate of at least approximately 10 cc per 100 in$^2$ per 24 hrs. at 23° C., 100% ΔH$_2$. Finally, the container may be configured to allow ingress or egress of water vapor into or from the compartment at a rate of less than approximately 0.030 g H$_2$O per 100 in$^2$ per 24 hrs. at 38° C., 90% ΔRH.

The optimizations described above prevent hydrogen from accumulating and causing the compartment of the container holding the air-activated heating material to swell and also minimize the egress of water vapor and the ingress of oxygen. Consequently, these parameters make embodiments of the present invention useful for the storage and quick preparation of food.

Certain embodiments of a container 10 have been illustrated, but the invention is not limited to these types. Indeed, embodiments of the invention can be applied to any container that includes an air-activated material as a self-contained heating element for producing heat, such as to heat contents packaged within the container. For example, in some embodiments, the container may be configured as described above and shown in FIGS. 1-6, wherein at least a portion of the first film layer of the first web is configured to be separated from the second film layer to reveal a plurality of openings in the first film layers so as to allow air to enter the compartment. The first film layer of the first web may comprise at least one score line defining at least one peelable portion of the first film layer that is configured to be separated from the second film layer, and the at least one score line of the first film layer, the adhesive layer, and the score lines of the second film layer may define a plurality of tortuous paths through a thickness of the first web configured to allow hydrogen gas to escape from the compartment. Moreover, the first film layer of the first web may define the openings, wherein the second film layer is configured to cover the openings when the second film layer is adhered to the first film layer. In other embodiments, the container may be configured such that the first film layer of the first web defines the openings (e.g., there are no plugs), and the second film layer is configured to cover the openings when the second film layer is adhered to the first film layer.

Furthermore, embodiments of the invention may be used to heat other items, such as items or objects not necessarily stored or pre-packaged within the container.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A container comprising:
    a first web comprising a laminate of a first film layer and a second film layer, wherein the first film layer is adhered via an adhesive layer to the second film layer;
    a second web peripherally sealed to the first web so as to form a compartment therebetween; and
    an air-activated material disposed within the compartment, wherein at least a portion of the first film layer of the first web is configured to be separated from the second film layer to reveal a plurality of openings in the first film layer so as to allow air to enter the compartment,
    wherein the air-activated material is configured to react with the air entering the compartment via the openings to activate the material, and
    wherein prior to separation of the second film layer from the first film layer, the container is configured to allow ingress of oxygen into the compartment at a rate less than approximately 3 cc per 100 in$^2$ per 24 hrs. at 23° C.

2. The container of claim 1, wherein prior to the separation of the second film layer from the first film layer, the container is configured to allow egress of hydrogen from the container at rate of at least approximately 10 cc per 100 in$^2$ per 24 hrs. at 23° C.

3. The container of claim 1, wherein prior to the separation of the second film layer from the first film layer, the container is configured to allow ingress or egress of water vapor into or out of the compartment at a rate of less than approximately 0.030 g per 100 in$^2$ per 24 hrs. at 38° C.

4. The container of claim 1, wherein the second film layer of the first web comprises a plurality of score lines defining plugs, wherein the plugs are configured to be separated and displaced from the second film layer upon separation of the respective portion of the first film layer to create the openings in the second film layer.

5. The container of claim 4, wherein the first film layer of the first web comprises at least one score line defining at least one peelable portion of the first film layer that is configured to be separated from the second film layer, and wherein the at least one score line of the first film layer, the adhesive layer, and the score lines of the second film layer define a plurality of tortuous paths through a thickness of the first web configured to allow hydrogen gas to escape from the compartment.

6. The container of claim 1, wherein the first film layer of the first web defines the openings, wherein the second film layer is configured to cover the openings when the second film layer is adhered to the first film layer.

7. A container comprising:
a first web comprising a laminate of a first film layer and a second film layer, wherein the first film layer is adhered via an adhesive layer to the second film layer;
a second web peripherally sealed to the first web so as to form a compartment therebetween; and
an air-activated material disposed within the compartment,
wherein at least a portion of the first film layer of the first web is configured to be separated from the second film layer to reveal a plurality of openings in the first film layer so as to allow air to enter the compartment,
wherein the air-activated material is configured to react with the air entering the compartment via the openings to activate the material, and
wherein prior to separation of the second film layer from the first film layer, the container is configured to allow egress of hydrogen from the container at rate of at least approximately 10 cc per 100 in$^2$ per 24 hrs. at 23° C.

8. The container of claim 7, wherein prior to the separation of the second film layer from the first film layer, the container is configured to allow ingress of oxygen into the compartment at a rate less than approximately 3 cc per 100 in$^2$ per 24 hrs. at 23° C.

9. The container of claim 7, wherein prior to the separation of the second film layer from the first film layer, the container is configured to allow ingress or egress of water vapor into or out of the compartment at a rate of less than approximately 0.030 g per 100 in$^2$ per 24 hrs. at 38° C.

10. The container of claim 7, wherein the second film layer of the first web comprises a plurality of score lines defining plugs, wherein the plugs are configured to be separated and displaced from the second film layer upon separation of the respective portion of the first film layer to create the openings in the second film layer.

11. The container of claim 10, wherein the first film layer of the first web comprises at least one score line defining at least one peelable portion of the first film layer that is configured to be separated from the second film layer, and wherein the at least one score line of the first film layer, the adhesive layer, and the score lines of the second film layer define a plurality of tortuous paths through a thickness of the first web configured to allow hydrogen gas to escape from the compartment.

12. The container of claim 7, wherein the first film layer of the first web defines the openings, wherein the second film layer is configured to cover the openings when the second film layer is adhered to the first film layer.

13. A container comprising:
a first web comprising a laminate of a first film layer and a second film layer, wherein the first film layer is adhered via an adhesive layer to the second film layer;
a second web peripherally sealed to the first web so as to form a compartment therebetween; and
an air-activated material disposed within the compartment,
wherein at least a portion of the first film layer of the first web is configured to be separated from the second film layer to reveal a plurality of openings in the first film layer so as to allow air to enter the compartment,
wherein the air-activated material is configured to react with the air entering the compartment via the openings to activate the material, and
wherein prior to separation of the second film layer from the first film layer, the container is configured to allow ingress or egress of water vapor into or out of the compartment at a rate of less than approximately 0.030 g per 100 in$^2$ per 24 hrs. at 38° C.

14. The container of claim 13, wherein prior to the separation of the second film layer from the first film layer, the container is configured to allow ingress of oxygen into the compartment at a rate less than approximately 3 cc per 100 in$^2$ per 24 hrs. at 23° C.

15. The container of claim 13, wherein prior to the separation of the second film layer from the first film layer, the container is configured to allow egress of hydrogen from the container at rate of at least approximately 10 cc per 100 in$^2$ per 24 hrs. at 23° C.

16. The container of claim 13, wherein the second film layer of the first web comprises a plurality of score lines defining plugs, wherein the plugs are configured to be separated and displaced from the second film layer upon separation of the respective portion of the first film layer to create the openings in the second film layer.

17. The container of claim 16, wherein the first film layer of the first web comprises at least one score line defining at least one peelable portion of the first film layer that is configured to be separated from the second film layer, and wherein the at least one score line of the first film layer, the adhesive layer, and the score lines of the second film layer define a plurality of tortuous paths through a thickness of the first web configured to allow hydrogen gas to escape from the compartment.

18. The container of claim 13, wherein the first film layer of the first web defines the openings, wherein the second film layer is configured to cover the openings when the second film layer is adhered to the first film layer.

* * * * *